United States Patent [19]

Ewen et al.

[11] Patent Number: 5,688,735
[45] Date of Patent: Nov. 18, 1997

[54] METHOD FOR CONTROLLING THE MELTING POINTS AND MOLECULAR WEIGHTS OF SYNDIOTACTIC POLYOLEFINS USING METALLOCENE CATALYST SYSTEMS

[75] Inventors: John A. Ewen, Houston; B. R. Reddy, Baytown, both of Tex.; Michael J. Elder, Raleigh, N.C.

[73] Assignee: Fina Technology, Inc., Dallas, Tex.

[21] Appl. No.: 471,055

[22] Filed: Jun. 6, 1995

Related U.S. Application Data

[62] Division of Ser. No. 903,058, Jun. 22, 1992.
[51] Int. Cl.[6] ............................................. C08F 4/64
[52] U.S. Cl. ...................... 502/117; 502/152; 502/155; 526/127; 526/160; 526/943
[58] Field of Search ........................... 502/117, 152, 502/155; 526/160

[56] References Cited

U.S. PATENT DOCUMENTS 4,794,096  12/1988  Ewen ............................. 502/117
5,436,305   7/1995  Alt et al. ....................... 526/160

FOREIGN PATENT DOCUMENTS 4-69394   3/1992   Japan .

*Primary Examiner*—David W. Wu
*Attorney, Agent, or Firm*—Jim Wheelington; M. Norwood Cheairs

[57] ABSTRACT

This invention is for a method for varying the melting points and molecular weights of syndiotactic polyolefins by using metallocene catalysts with substituents on the aryl rings of a fluorene ligand in certain positions. Electron donating substituents, for example, dialkylamino, halogen, and alkoxy groups, when present on fluorene at C1, C2, C3 or C2 and C7 render the catalyst less active and decrease the polymer molecular weight. Electron donating substituents, such as alkyl, dialkylamino, halogen or alkoxy, at C4 not only increased the catalyst efficiency but also dramatically increased the polymer molecular weight. Bulky hydrocarbyl substituents, such as alkyl, cycloalkyl and aryl groups, at C2 and C7 increase the melting point. Bulky substituents such as hydrocarbyl groups like alkyl, cycloalkyl, aryl, alkoxy and dialkylamino groups etc., at C4/C5 decrease the melting point. When multiple substituents are present on fluorene, their effects are additive.

45 Claims, No Drawings

METHOD FOR CONTROLLING THE MELTING POINTS AND MOLECULAR WEIGHTS OF SYNDIOTACTIC POLYOLEFINS USING METALLOCENE CATALYST SYSTEMS

This is a Divisional application of co-pending application Ser. No. 07/903,058, filed on Jun. 22, 1992.

BACKGROUND OF THE INVENTION

1. Technical Field

The present invention provides a method for varying the melting points and molecular weights of syndiotactic polyolefins in a process of polymerization using metallocene catalysts. The catalysts used in the present invention are stereorigid and include a bridge between sterically different cyclopentadienyl groups. It has been discovered that addition of substituents in the aryl rings in the fluorene ligand of one cyclopentadienyl ring influences melting point and molecular weight of syndiotactic polyolefins produced with these metallocene catalysts.

The present invention relates to the use of metallocene catalysts in the production of polyolefins, particularly polypropylene, and the ability to vary certain properties of the polymer products by varying the structure of the catalyst. In particular, it has been discovered that position of substituents on the aryl rings of fluorene ligand in the metallocene catalyst changes the melting points and the molecular weights of the polymer products.

2. Description of the Prior Art

Transition metal catalysts in the form of metallocenes have been known for some time, but up until just recently, such catalysts could only produce predominantly atactic polymer which is not nearly as useful as the crystalline forms, isotactic and syndiotactic polymers. It was discovered that by attaching a bridge between the cyclopentadienyl rings in a metallocene catalyst and by adding one or more substituents on the rings to make the compound both stereorigid and chiral, a high percentage of isotactic polymer could be produced. On the other hand, stereorigid metallocenes derived from achiral ligands containing differently substituted cyclopentadienyl rings connected by a bridge produced a high percentage of syndiotactic polymer.

The use of metallocenes as catalysts for the polymerization of ethylene is known in the art. German patent application 2,608,863 discloses a catalyst system for the polymerization of ethylene consisting of bis(cyclopentadienyl)-titanium dialkyl, an aluminum trialkyl and water. German patent application 2,608,933 disclosed an ethylene polymerization catalyst system consisting of zirconium metallocenes of the general formula (cyclopentadienyl)$_n$ Zr Y$_{4-n}$, wherein Y represents R$_1$CH$_2$AlR$_2$, CH$_3$CH$_2$AlR$_2$ and CH$_3$CH (AlR$_2$)$_2$ wherein R stands for an alkyl or metallo-alkyl, and n is a number within the range 1–4; and the metallocene catalyst is in combination with an aluminum trialkyl cocatalyst and water.

The use of metallocenes as catalysts in the copolymerization of ethylene and other alpha-olefins is also known in the art. U.S. Pat. No. 4,542,199 to Kaminsky, et al. disclosed a process for the polymerization of olefins and particularly for the preparation of polyethylene and copolymers of polyethylene and other alphaolefins. The disclosed catalyst system includes a catalyst of the formula (cyclopentadienyl)$_2$MeRHal in which R is a halogen, a cyclopentadienyl or a C$_1$–C$_6$ alkyl radical, Me is a transition metal, in particular zirconium, and Hal is a halogen, in particular chlorine. The catalyst system also includes an aluminoxane having the general formula Al$_2$OR$_4$(Al(R)-O)$_n$ for a linear molecule and/or (Al(R)-O)$_{n+2}$ for a cyclic molecule in which n is a number from 4–20 and R is a methyl or ethyl moiety. A similar catalyst system is disclosed in U.S. Pat. No. 4,404,344.

U.S. Pat. No. 4,530,914 discloses a catalyst system for the polymerization of ethylene to polyethylene having a broad molecular weight distribution and especially a bimodal or multimodal molecular weight distribution. The catalyst system is comprised of at least two different metallocenes and an alumoxane. The patent discloses metallocenes that may have a bridge serving to make the rings stereorigid. The bridge is disclosed as being a C$_1$–C$_4$ alkylene radical, a dialkyl germanium or silicon, or an alkyl phosphine or amine radical.

European Patent Application 0185918 discloses a stereorigid, chiral metallocene catalyst for the polymerization of olefins. The bridge between the cyclopentadienyl groups is disclosed as being a linear hydrocarbon with 1–4 carbon atoms or a cyclical hydrocarbon with 3–6 carbon atoms. The application discloses zirconium as the transition metal used in the catalyst, and linear or cyclic alumoxane is used as a co-catalyst. It is disclosed that the system produces a polymer product with a high isotactic index.

It is known that polyolefins, and principally polypropylene, may be produced in three primary forms: isotactic, syndiotactic and atactic, the first two being crystalline and the latter being amorphous. While it is possible for a catalyst to produce all three types of polymer, it is desirable for a catalyst to produce predominantly isotactic or syndiotactic polymer with very little atactic polymer. U.S. Pat. No. 4,892,851 discloses a metallocene catalyst for use in preparing syndiotactic polyolefins. The catalyst comprises a bridged metallocene in which one of the cyclopentadienyl rings is substituted in a substantially different manner from the other ring. It was discovered that this type of catalyst is highly syndiospecific, and it also produces a polymer with a novel microstructure. The invention further includes the use of one or more of the catalysts in a polymerization process. The catalyst is generally described by the formula:

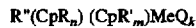

wherein each Cp is a cyclopentadienyl or substituted cyclopentadienyl ring; each R$_n$ and R'$_m$ is the same or different and is a hydrocarbyl radicals having 1–20 carbon atoms; R" is a structural bridge between the two Cp rings imparting stereorigidity to the catalyst; Me is a group 4b, 5b, or 6b metal from the Periodic Table of Elements; each Q is a hydrocarbyl radical having 1–20 carbon atoms or is a halogen; 0≦k≦3; 1≦m≦4; 0≦n≦4 and wherein R'$_m$ is selected such that (CpR'$_m$) is a sterically different ring than (CpR$_n$). The present invention further discloses that the catalyst structure affects the properties of a syndiotactic polymer. It is believed the invention would be effective for all predominantly crystalline polymer from olefins of three or more carbon atoms.

The present invention relates to discoveries made as to varying substituents added to the aryl rings in the fluorene ligand in a metallocene catalyst on the polymerization of propylene and higher alpha-olefins. In particular, it was discovered that by varying these components, the physical properties of the polymer may be controlled.

SUMMARY OF THE INVENTION

It was discovered that the addition of various substituents on the aryl rings of the fluorene ligand varied the melting point of a polyolefin. This is a significant discovery, as heretofore it was the commercial practice to vary the melting points of polymer products by co-polymerizing varying amounts of ethylene to produce co-polymers with a range of differing melting points. It is desirable to produce a homopolymer with varying melting points without the use of ethylene. The present invention provides a method for the production of homo-polymers with varying melting points by varying the structure of the metallocene catalyst used in the polymerization.

Similarly, it was discovered that by changing the substituents on the aryl rings of the fluorene ligand of a metallocene catalyst, polymers are produced with different molecular weights. Thus, the molecular weight of the polymer product may be controlled by changing the substituents in the catalyst. Accordingly, the present invention provides a method for varying both the melting point and the molecular weight of a polymer product.

The present invention also provides a process for the polymerization of olefins comprising contacting an organoaluminum compound with a metallocene described by the formula:

wherein $(C_5H_4)$ is a cyclopentadienyl ring; $(C_4H_{4-m}R'_mC_5C_4H_{4-n}R'_n)$ is a substituted cyclopentadienyl ring, preferably a fluorenyl radical; R' is a hydrocarbyl radical having from 1–20 carbon atoms, a halogen, an alkoxy, an alkoxy alkyl or an alkylamino radical, each R' may be the same or different; R" is a structural bridge between the $(C_5H_4)$ and $(C_4H_{4-m}R'_mC_5C_4H_{4-n}R'_n)$ rings to impart stereorigidity and, preferably, is an alkylene radical having 1–4 carbon atoms, a silicon hydrocarbyl compound, a germanium hydrocarbyl compound, an alkyl phosphine, an alkyl amine, a boron compound or an aluminum compound and may contain any of these and other hydrocarbyl groups to form the bridge; Q is a hydrocarbon radical such as an alkyl, aryl, alkenyl, alkylaryl or arylalkyl radical having 1–20 carbon atoms or is a halogen; Me is a Group IIIB, IVB, VB, or VIB metal as positioned in the Periodic Table of Elements; $1 \leq m \leq 4$; $0 \leq n \leq 4$; and p is the valence of Me minus 2.

The metallocene structure is given below:

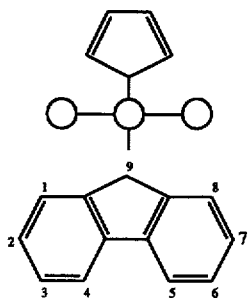

The preferred positions of R' include C1, C2, C3, C4; C1, C8; C2, C7; C3, C6; and C4, C5. The selection of substituents for fluorene is based on the steric bulk as well as their ability to donate or withdraw electrons, either inductively or through resonance. These substituents include alkyl and aryl groups, alkylamino groups and alkyl derivatives containing Group IVB elements such as silicon, germanium and tin.

An olefin monomer is added to the metallocene catalyst and the organoaluminum compound. After the polymerization has taken place, the polymer product is withdrawn. The process is characterized by the fact that it provides control of the melting point of the polymer product by controlling the number of inversions in the xylene insoluble fraction of the polymer. The number of inversions are effected by the R' group. Thus, the melting point of the polymer product may be varied and controlled by varying the R' substituents on the aryl rings of the fluorene ligand of the metallocene.

It was discovered that for a given substituent on the fluorene, the polymer yield (catalyst efficiency) and polymer properties, such as melting point and molecular weight, depended on the site of substitution. It was also discovered that for a given site of substitution on fluorene, the polymer yield and the polymer properties, such as molecular weight and melting point, depended on the nature of the substituents. Furthermore, it was discovered that the effects on polymer properties of different kinds of substituents on the fluorene ring are additive.

DETAILED DESCRIPTION OF THE INVENTION

The present invention provides a method of controlling the melting point of a polymer by controlling the number of inversions in the chain of the xylene insoluble fraction of the polymers. The number of inversions are controlled in turn by the structure and composition of the catalyst, and the number of inversions and hence the melting point of the polymer product may be controlled and varied by varying the catalyst. In particular, it has been discovered that varying the R' substituents on the aryl rings of the fluorene ligand will vary the melting point. In addition, it has been discovered that varying the substituents on the aryl rings of the fluorene ligand in the catalyst will also vary the molecular weights of the polymer products. These beneficial advantages will become more apparent from the following detailed description of the invention and the accompanying examples.

Normally, when propylene, or another alpha-olefin, is polymerized with a catalyst system prepared from a transition metal compound, the polymer comprises a mixture of crystalline hydrocarbon insoluble and amorphous hydrocarbon soluble fractions which may be separated using suitable solvents. As described by the present invention, the composition and location of the substituents added to the ligand affect the properties of the polymer such as melting points and molecular weights.

The metallocene catalyst as used in the present invention must be stereorigid but may be chiral or achiral. Rigidity is achieved by an interannular bridge. The catalyst may be described by the formula:

wherein $(C_5H_4)$ is a cyclopentadienyl ring and $(C_4H_{4-m}R'_mC_5C_4H_{4-n}R'_n)$ is a substituted cyclopentadienyl ring; R' is a hydrocarbyl radical, halogen, an alkoxy, an alkoxy alkyl or an alkylamino radical having from 1–20 carbon atoms, each R' may be the same or different; R" is a structural bridge between the $(C_5H_4)$ and $(C_4H_{4-m}R'_mC_5C_4H_{4-n}R'_n)$ rings to impart stereorigidity and, preferably, is an alkylene radical having 1–4 carbon atoms, or arylaklyl or diaryl alkyl radical contains 7–20 atoms, a silicon hydrocarbyl compound, a germanium hydrocarbyl compound, an alkyl phosphine, or an alkyl amine; Q is a hydrocarbon radical, such as an alkyl, aryl, alkenyl, alkylaryl or arylalkyl radical having 1–20 carbon atoms, or is a halogen; Me is a Group IIIB, IVB, VB, or VIB metal as positioned in the Periodic Table of Elements; $1 \leq m \leq 4$; $0 \leq n \leq 4$; and p is the valence of Me minus 2.

Exemplary alkylene radicals having 1–4 carbon atoms are methylene, ethylene, propylene and butylene. Exemplary hydrocarbyl radicals are methyl, ethyl, propyl, butyl, amyl, isoamyl, hexyl, isobutyl, heptyl, octyl, nonyl, decyl, cetyl, phenyl, and the structural isomers of the alkyl groups where appropriate. Exemplary halogen atoms are fluorine, chlorine, bromine and iodine with fluorine and chlorine being preferred.

The preferred transition metals are Group IVB metals, such as titanium, zirconium and hafnium. Q is preferably a methyl radical or chlorine and p is preferably 2. ($C_4H_{4-m}R'_mC_5C_4H_{4-n}R'_n$) preferably forms an fluorenyl radical. As indicated, other hydrocarbon groups may be added to the cyclopentadienyl rings. The present invention is such that the R' substituents may be varied among any of those compounds listed in the above formula so as to provide polymer products with different properties. The preferred R" bridge components are alkenyl radicals, such as methylene, ethylene and isopropyl; diarylmethyl, such as diphenylmethyl; an alkyl silicon or a cycloalkyl silicon, such as cyclopropyl silicon, with the most preferred being isopropyl or diphenylmethyl.

The metallocene catalysts used in the present invention are produced using methods known in the art. The catalyst synthesis generally involves the following multi-step synthesis sequence: a) preparation of substituted fluorene; b) preparation of the ligand; c) preparation of the metallocene. Substituted fluorenes were prepared according to the published literature procedures whenever such fluorenes were not commercially available. For example, 4-methoxyfluorene, 2-dimethylaminofluorene, 2,7-dichlorofluorene, 2,7-difluorofluorene, and methylenephenanthrene were purchased from Aldrich Chemical Company. 2,7-bis(dimethylaminofluorene) was prepared from the commercially available 2,7-diaminofluorene and trimethylphosphite using the procedure described in "J. Chem. Soc.", 2034 (1953); J. Chem. Soc., 870 (1954); and Vogel's "Text Book of Practical Organic Chemistry", 4th Edn, 1978 (p. 671). Conversion of commercially available 1-, 2-, and 3-hydroxyfluorenes to their methoxy derivatives was accomplished by reacting them with dimethyl sulphate in dimethyl sulfoxide in the presence of aqueous sodium-hydroxide as described in Vogel's "Text Book of Practical Organic Chemistry", 4th Edn, 1978, P 755. 2-hydroxyfluorene was also synthesized by hydrogenation of 2-hydroxy fluorenone in the presence of 10% Pd on carbon in ethanol containing p-toluene sulfonic acid. Synthesis of 4-methyl fluorene was accomplished in two steps using standard organic transformations known in the art. First, 4-carboxyfluorene was reacted with lithium aluminum hydride to obtain 4-hydroxymethyl fluorene which was hydrogenated in ethanol in the presence of 10% Pd on carbon to give 4-methyl fluorene. Reaction of 4-hydroxymethyl fluorene described above with sodium hydride in THF followed by reaction of the sodium alkoxide with methyl iodide gave 4-methylenemethoxy fluorene. Synthesis of 2,7-dimethylfluorene from 5-methylanthranilic acid in several steps was accomplished using the procedures described in references "J. Am. Chem. Soc." 75, 2663 (1953) and "Ohio. J. Sci.", 55, 187 (1965). Preparation of 2,7- di-t-butyl-4-methoxy fluorene from 4-methoxy fluorene was achieved by reacting the latter with 2,6-di-t-butyl-p-cresol in the presence of aluminum chloride in nitromethane as described in the reference, "Synthesis", 336 (1984). Preparation of 2,7-di-t-butylfluorene was accomplished by reacting fluorene with 2,7-di-t-butyl-p-cresol in the presence of aluminum chloride in nitromethane as described in the reference synthesis, 336(1984). Synthesis of 2,7-di-t-butylethynylfluorene was achieved by reacting 2,7-diiodofluorene with t-butylacetylene in the presence of organopalladium catalysts as described for similar systems in "Journal of Organic Chemistry", 48, 1854–1862, 1983.

The synthesis of the bridged, substituted dicyclopentadienyl ligand was accomplished by contacting fulvene or substituted fulvene with alkali metal salt of a substituted cyclopentadienyl compound of the general formula $M[C_4H_{4-m}R'_mC_5C_4H_{4-n}R'_n]$ where M is Group I metal, to produce a bridged substituted dicyclopentadiene hereafter referred to as the ligand. As known in the art, fulvene is Cp=C in which a carbon atom is bound by a double bond to a cyclopentadienyl ring. Substituted fulvene as used herein is intended to mean Cp=CR'$_a$ wherein fulvene is substituted at the terminal carbon atom with R'$_a$ being the same or different. Conversion of the ligands to the metallocenes were performed under an inert gas atmosphere using a Vacuum Atmospheres Dry box or Shlenk techniques. The solvents were predried and distilled under an inert atmosphere. The experimental procedure was described in the literature in "J. Am Chem. Soc.", 110, 6255 (1988)

The following Examples illustrate methods of catalyst synthesis and procedures for obtaining a metallocene with various substituents on the fluorenyl ring. The Examples use various zirconocenes and hafnocenes to illustrate the invention but similar results would be expected for titanocene and other metallocene catalysts.

EXAMPLE 1 iPr (4-OCH$_3$Flu) (Cp) ZrCl$_2$

To a solution of iPr[4-OCH$_3$Flu)Cp] (2.84 g, 9.4 mmol) in 50 ml ether methyllithium in ether (1.4M, 20.7 mmol) was added at room temperature and stirred for two hours. Approximately 10 ml dry tetrahydrofuran (THF) were added and stirred overnight. Pentane (100 ml) was added to precipitate all the dianion and the solvents were cannulated out. The solvent traces were removed under vacuum. The residual solid was cooled to –78° C. and methylene chloride, prechilled to –78° C. (60 ml) was cannulated in. A slurry of zirconium tetrachloride (2.20 g) in methylene chloride (60 ml), prechilled to –78° C. was cannulated into the dianion solution. The reaction mixture was allowed to come to room temperature slowly and stirred overnight. The dark red solution was filtered and the filtrate was concentrated to 1/10 volume. A toluene/pentane mixture was added, to the concentrate which precipitated the product. The solvents were cannulated out, the product washed with toluene/pentane mixture and dried in vacuo.

EXAMPLE 2 iPr[2,7-(CH$_3$)$_2$Flu](Cp) ZrCl$_2$

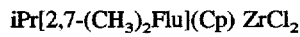

To an anhydrous ether (75 ml) suspension of iPr[(2,7-(CH$_3$)$_2$Flu)Cp] (3.0 g, 10 mmol), methyllithium in ether (1.4M, 22 mmol) was added and stirred for two to four hours. Anhydrous THF (10 ml) was added and stirred for eighteen hours. The dark red solution was concentrated and dry pentane was added resulting in an orange solid precipitate. The solid was washed with twice the pentane and was suspended in 120 ml fresh pentane. A slurry of ZrCl$_4$ in dry pentane was cannulated into the dianion suspension under argon pressure. After stirring for two hours, THF (5 ml) was added and the mixture stirred overnight. The organic layer was decanted and the solid was washed with dry pentane. The washed solid, was dissolved in dry methylene chloride and filtered. Removal of solvents from the filtrate yielded reddish orange solid. A portion of the solid was redissolved in dry methylene chloride, concentrated and cooled to −10° C. The precipitated solid was filtered, dried under vacuum and stored under nitrogen. Yield 20–40%.

EXAMPLE 3

Ph$_2$C{2,7-[C(CH$_3$)$_3$]$_2$Flu}(Cp)ZrCl$_2$

To a solution of (cyclopentadienyl) (9-[2,7-di-t-butylfluorenyl)diphenylmethane (4.0 g, 8.3 mmol) in 250 ml dry THF kept at −78° C., a solution of methyllithium in ether (1.4M, 11.8 ml, 16.5 mmol) was added dropwise and stirred overnight. The solvents were removed under vacuum and residual red oil was washed with a mixture of dry hexane/dry ether (10:1). The red dianion was reacted with ZrCl$_4$ and the crude catalyst purified as described in Example 1.

EXAMPLE 4 iPr (2-OCH$_3$Flu) (Cp) ZrCl$_2$

To a suspension of iPr[(2-OCH$_3$Flu)Cp] (1.68 g, 5.6 mmol) in dry THF (50 ml), methyllithium in ether (1.4M, 14.0 mmol) was added and stirred at room temperature. The solvents were removed under vacuum and the residue washed with ether/pentane mixture to obtain the dianion as a dark red solid. The subsequent reaction with ZrCl$_4$ was performed under conditions described in Example 1.

EXAMPLE 5 iPr (1-OCH$_3$Flu) (Cp) ZrCl$_2$ iPr[(1-OCH$_3$Flu)Cp] was converted to iPr[(1-OCH$_3$Flu)Cp]ZrCl$_2$ using the procedure described in Example 2. The crude product was recrystallized from toluene to obtain a pink solid.

EXAMPLE 6 iPr (3-OCH$_3$Flu) (Cp) ZrCl$_2$ iPr[(3-OCH$_3$Flu)Cp] was converted to iPr[(3-OCH$_3$Flu)Cp]ZrCl$_2$ using the procedure described in Example 2. The crude product was recrystallized from toluene.

EXAMPLE 7 iPr(4-CH$_2$OCH$_3$Flu)(Cp)ZrCl$_2$ iPr[(4-CH$_2$OCH$_3$Flu) Cp] was converted to iPr[(4-CH$_2$OCH$_3$Flu)Cp]ZrCl$_2$ using the procedure in Example 2.

EXAMPLE 8 iPr(4-N(CH$_3$)$_2$Flu) (Cp) ZrCl$_2$ iPr[4-N(CH$_3$)$_2$Flu)Cp] was converted to iPr[4-N(CH$_3$)$_2$Flu]ZrCl$_2$ using the procedure described in Example 2.

EXAMPLE 9 iPr (2-N(CH$_3$)$_2$Flu) (Cp) ZrCl$_2$ iPr[(2-N(CH$_3$)$_2$Flu) Cp]ZrCl$_2$ was prepared from the corresponding ligand according to the procedure described in Example 2.

EXAMPLE 10 iPr(4-CH$_3$Flu)(Cp)ZrCl$_2$ iPr[(4-CH$_3$Flu)Cp] was reacted with ZrCl$_4$ using the procedure described in Example 1. The impure iPr[(4-CH$_3$Flu)Cp]ZrCl$_2$ was purified by washing the sample repeatedly with toluene followed by extraction with toluene/methylene chloride, filtration and removal of solvents.

EXAMPLE 11 iPr (2,7-Cl$_2$Flu) (Cp) ZrCl$_2$ iPr[(2,7-Cl$_2$Flu)Cp] (3.6 g, 10.6 mmol) was dissolved in dry ether (100 ml) and cooled to 0° C. Methyllithium in ether (1.4M, 17 ml, 23.8mmol) was added and stirred at 0° C. until gas evolution had ceased. The solution was allowed to come to room temperature and stirred overnight. The ether solution was concentrated and 90 ml hexane was added. Red glueish residue was obtained which was washed with ether/hexane. The solvents were removed under vacuum. The solid dianion obtained was reacted with ZrCl$_4$ using the procedure described in Example 1.

EXAMPLE 12 iPr{2,7-[N(CH$_3$)$_2$]$_2$Flu}(Cp) ZrCl$_2$ iPr[(2,7-(N(CH$_3$)$_2$)$_2$Flu)Cp] (2.63 g, 7.3 mmol) was suspended in dry ether (55 ml) and methyllithium in ether (1.4M, 16.1mmol) was added and stirred overnight. Additional ether (25–30 ml) was added to the resulting suspension and the solvent was cannulated out. The solid was washed with pentane and suspended in fresh pentane (125 ml). Subsequent procedure was identical to that described in Example 2.

EXAMPLE 13 iPr(2,7-[N(CH$_3$)$_2$]Flu) (Cp) Zr(CH$_3$)$_2$ iPr[(2,7-(N(CH$_3$)$_2$)$_2$Flu) Cp]ZrCl$_2$ was converted to iPr[(2,7-(N(CH$_3$)$_2$)Flu)Cp]Zr(CH$_3$)$_2$ by reacting the crude dichloro complex containing lithium chloride with methyl magnesium chloride in THF.

EXAMPLE 14 iPr{4-OCH$_3$-2,7-[C(CH$_3$)$_3$]$_2$Flu}(Cp) ZrCl$_2$

To a solution of iPr[(2,7-di-t-butyl-4-OCH]Flu)Cp] (1.3 g, 3.1 mmol) in ether (40 ml), methyllithium in ether (1.4M, 6.5 mmol) was added and stirred overnight. The solvents were removed under vacuum and hexane (100 ml) was added. The supernatant was removed and the residue was washed with hexane. From the hexane washes 0.8 g of the unreacted material was recovered. The hexane insoluble residue was suspended in hexane and an amount of ZrCl$_4$ equivalent to the reacted starting ligand was added and then stirred overnight. The supernatant was cannulated out and the residue washed with hexane. The residual black solid was dissolved in dry methylene chloride and filtered. Removal of the solvent yielded a dark green solid, which by HNMR, was found to be a mixture of the dichloride, monomethyl chloride and the dimethyl derivatives of the target complex.

EXAMPLE 15 iPr (4-OCH$_3$Flu) (Cp) HfCl$_2$

The reaction of iPr[(4-OCH$_3$Flu)Cp] with HfCl$_4$ to obtain iPr[(4-OCH$_3$Flu)Cp]HfCl$_2$ was performed as described in Example 1 by using HfCl$_4$ instead of ZrCl$_4$.

EXAMPLE 16 iPr (2,7-F$_2$Flu) (Cp) ZrCl$_2$

The reaction of iPr(2,7-F$_2$Flu) (Cp) with ZrCl$_4$ to obtain iPr(2,7-F$_2$Flu) (Cp)ZrCl$_2$ was done as described in example

EXAMPLE 17 iPr(2,7-(C≡CC(CH₃)₃Flu) (Cp) ZrCl₂

The reaction of iPr (2,7-(C≡CC(CH₃)₃Flu) (Cp) with ZrCl₄ was done by the addition of 2.2 equivalents of n-butyllithium to an ether solution of the ligand and stirred overnight. The ether was evaporated under a slow stream of argon. The resulting purple solid was washed with hexane twice and suspended in a fresh batch of hexane. A slurry of ZrCl₄ in hexane was added and stirred overnight. The hexane was removed by cannulation, the resulting solid washed with hexane, dried under vacuum. The purification procedure was identical to that described in Example 16.

iPr(4-OCH₃Flu)(Cp)ZrCl₂-isopropyl(4-methoxyfluorenyl) (cyclopentadienyl)zirconium dichloride iPr[2,7-(CH₃)₂Flu](Cp) ZrCl₂-isopropyl(2,7-dimethylfluorenyl) (cyclopentadienyl)zirconium dichloride Ph₂C(2,7-[C(CH₃)₃]₂Flu)(Cp)ZrCl₂-diphenylmethyl(2,7-di-t-butyl-fluorenyl)(cyclopentadienyl)zirconium dichloride iPr(2-OCH₃Flu)(Cp)ZrCl₂- isopropyl(2-methoxyfluorenyl) (cyclopentadienyl)zirconium dichloride iPr(1-OCH₃Flu)(Cp)ZrCl₂-isopropyl(1-methoxyfluorenyl) (cyclopentadienyl)zirconium dichloride iPr(3-OCH₃Flu)(Cp)ZrCl₂-isopropyl(3-methoxyfluorenyl) (cyclopentadienyl)zirconium dichloride iPr(4-CH₂OCH₃Flu)(Cp)ZrCl₂-isopropyl(4-methoxymethyl-fluorenyl)(cyclopentadienyl)zirconium dichloride iPr(4-[N(CH₃)₂]Flu)(Cp)ZrCl₂-isopropyl(4-dimethylaminofluorenyl) (cyclopentadienyl) zirconium dichloride iPr(2-N(CH₃)₂Flu)(Cp)ZrCl₂-isopropyl(2-dimethylaminofluorenyl) (cyclopentadienyl)zirconium dichloride iPr(4-CH₃Flu)(Cp)ZrCl₂-isopropyl(4-methylfluorenyl) (cyclopentadienyl)zirconium dichloride iPr(2,7-Cl₂Flu)(Cp)ZrCl₂-isopropyl(2,7-dichlorofluorenyl) (cyclopentadienyl)zirconium dichloride iPr{2,7-[C(CH₃)₃]₂Flu}(Cp)ZrCl₂-isopropyl(2,7-bis-di-t-butylfluorenyl)(cyclopentadienyl)zirconium dichloride iPr(2,7-[N(CH₃)₂]₂Flu) (Cp) Zr(CH₃)₂-isopropyl (2,7-bis-di-methylaminofluorenyl) (cyclopentadienyl)zirconium dimethyl iPr(4-OCH₃ 2,7-[N (C(CH₃)₃]₂Flu) (Cp) ZrCl₂-isopropyl (4-methoxy 2,7 -di-methylaminofluorenyl) (cyclopentadienyl)zirconium dichloride iPr(4-OCH₃Flu) (Cp) HfCl₂-isopropyl (4-methoxyfluorenyl) (cyclopentadienyl) hafnium dichloride iPr (2,7 -F₂Flu) (Cp) ZrCl₂-isopropyl (2,7-difluorofluorenyl) (cyclopentadienyl)zirconium dichloride iPr (2,7-(C≡CC(CH₃)₃)₂Flu) (Cp) ZrCl₂-isopropyl (2,7-di (t-butylethnyl) fluorenyl) (cyclopentadienyl)zirconium dichloride The metallocene catalysts Just described are used in combination with an organoaluminum compound as a co-catalyst. Preferably, the organoaluminum compound is an alumoxane represented by the general formula (R-Al-O)ₙ in the cyclic form and R(R-Al-O)ₙAlR₂ in the linear form. In the general formula, R is an alkyl group with 1–5 carbons and n is an integer from 1 to about 20. Most preferably, R is a methyl group. Generally, in the preparation of alumoxanes from, for example, trimethyl aluminum and water, a mixture of the linear and cyclic compounds are obtained.

An alternative to the use of the organoaluminum compound is a catalyst system of a metallocene, neutral Lewis acid or ionic ionizing agent and, optionally, an aluminum alkyl. Methods for preparing a cationic metallocene catalyst system are disclosed in European Patent Application Nos. 90870176.6 (Publication no. 0427697A2) and 908701.8 (Publication no. 0426638A2), which are hereby incorporated by reference. The ionizing agent which is an ion pair converts the metallocene to a cation. The metallocene cation forms on ion pair with the anion component of the ionizing agent. The segment of the metallocene compound removed by ionization forms an anion which associates with the cation component of the ionizing agent. The ion pair formed from the anjou of the segment of metallocene and the cation of ionizing agent is chemically inert and non-reactive with regard to the metallocene cation and the metallocene cation-ionizing agent anion ion pair which is an active catalyst for polymerization of olefins.

An aluminum alkyl, such as triethylaluminum, is useful in such an ionic catalyst system to improve yields. It is believed that aluminum alkyl acts to enhance the ionizing process and to scavenge catalyst poisons.

The polymerization procedures useful in the present invention include any procedures known in the art. Generally, a metallocene compound as described above is selected, a catalyst is formed using the metallocene compound using any procedure known in the art, including those disclosed above, the catalyst is introduced into a polymerization reaction zone containing an olefin monomer of three or more carbon atoms, the reaction zone is maintained under polymerization reaction conditions and the polymer is extracted from the reaction zone.

In the Examples given below, four different polymerization procedures were utilized. These are just examples of possible polymerization procedures, as any known procedure may be used in practicing the present invention. These procedures, designated as A, B, C and D are described as follows:

POLYMERIZATION METHODS

Method A (Bulk polymerization)

The catalyst was dissolved in 5 mL of 10 wt % MAO in toluene, transferred to a stainless steel sample cylinder, and charged with 400 mL of propylene into an autoclave reactor containing 1000 mL of propylene stirring at room temperature. The catalyst was prepolymerized in situ by heating the reactor contents to 60° C. within 5 minutes. After stirring at 60° C. for one hour, the polymerization was terminated by rapidly venting the unreacted monomer and opening the reactor to the air. The contents of the reactor were dried in a vacuum oven prior to analysis.

Method B (Slurry polymerization)

The catalyst was dissolved in 2.5 milliliters of MAO. Another 2.5 milliliters of MAO were added to 500 Ml of toluene in a reactor. The catalyst solution was transferred to a stainless steel sample cylinder and charged into the reactor, containing the toluene thermostated at 30° C., with 100 psi of propylene. The contents of the reactor were stirred at 30° C. for one hour under 100 psi propylene pressure. At the end of this time polymerization was terminated by rapidly venting the reactor of unreacted monomer and opening the reactor to the air. Several hundred milliliters of methanol/4N HCl solution were added to the toluene slurry. The precipitated polymer was collected on a filter funnel and dried in a vacuum oven prior to analysis.

Method C

Bulk polymerization of 1.4 liter of propylene similar to Method A except that no MAO is used. Triphenylcarbenium tetrakis(pentafluorophenyl)boronate is used as an ionic ionizing agent to ionize a neutral metallocene and form a ion pair with the metallocene cation.

Triethylaluminum (TEA1) was dissolved in toluene and was added to a 2 liter Zipperclave reactor under 5 psig of nitrogen. One liter of propylene was pumped into the reactor. The mixture was stirred for ten minutes at 1200 rpm. Triphenylcarbenium tetrakis(pentafluorophenyl) boronate was dissolved in 10 ml of toluene. The metallocene was dissolved in 10 ml of toluene. The two solutions were mixed together for 5 minutes at room temperature. The catalyst mixture was added to a stainless steel bomb equipped with ball valves on each end. 400 ml of propylene were pumped through the bomb into the reactor. The contents of the reactor were agitated for sixty minutes. At the end of the polymerization, the reactor was cooled and the unreacted propylene was vented from the reactor. The reaction product was dried under vacuum. The polymer was then weighed and analyzed.

Method D

Bulk polymerization of 1.4 liter of propylene similar to Method A except that no MAO is used. N,N-dimethylanilinium tetrakis(pentafluorophenyl)boronate is used as an ionic ionizing agent to ionize a neutral metallocene and form a ion pair with the metallocene cation.

N,N-dimethylanilinium tetrakis(pentafluorophenyl) boronate was dissolved in 10 ml of toluene. The metallocene was dissolved in 10 ml of toluene. The two solutions were mixed together for 5 minutes at room temperature. One liter of propylene was pumped into the reactor. The catalyst mixture was added to a stainless steel bomb equipped with ball valves on each end. 400 ml of propylene were pumped through the bomb into the reactor. The contents of the reactor were agitated for sixty minutes. At the end of the polymerization, the reactor was cooled and the unreacted propylene was vented from the reactor. The reaction product was dried under vacuum. The polymer was then weighed and analyzed.

Polymerization results using metallocenes with various substituents are shown in Table I. The polymer product may be analyzed in various ways for differing properties. Particularly pertinent to the present invention are analyses for melting points and molecular weights.

The melting points in the examples below were derived from DSC (Differential Scanning Calorimetry) data as known in the art. The melting points reflected in the tables are not true equilibrium melting points but are DSC peak temperatures on "as-polymerized" samples previously heated to 450° K., held at this temperature for five minutes, and cooled at 10° K./minute with baseline correction. With syndiotactic polypropylene it is not unusual to get an upper and a lower peak temperature, i.e., two peaks, and the data reflects the higher peak melting point.

The molecular weights of the "as polymerized" polymers were calculated using GPC (Gel Permeation Chromatography) analysis and intrinsic viscosity (decaline solutions, 135° C.). From GPC, $M_w$, or the weight average molecular weight, and $M_n$, number average molecular weight, are obtained. $M_w$ divided by $M_n$ is a measurement of the breadth of the molecular weight distribution.

As known in the art, the molecular weight of a polymer is proportional to the rate of propagation of the polymer chain divided by the rate of termination of the chain. A change in the ratio leads to a change in the molecular weights. As described by the present invention, a change in the structure of the catalyst leads to a change in the ratio of the rates of polymerization as well as a change in the melting points of the polymer.

The invention having been generally described, the following table presents particular embodiments of the invention and demonstrates the practice and advantages thereof. It is understood that these embodiments are given by way of illustration and are not intended to limit the specification or the claims to follow in any manner.

TABLE I

| Catalyst (mg) | Substituent | Metal | MAO (ml) | Polymerization Temp (°C.) | Time (min) | Yield (g) | Method | Catalyst Efficiency (g/g · hr) | Melting Point (°C.)[a] | Molecular Weight* | NMR Data (%)[b] | | | |
|---|---|---|---|---|---|---|---|---|---|---|---|---|---|---|
| | | | | | | | | | | | mmmm | mmmr | xmrx | rrrr |
| 0.65 | H | Zr | 5 | 30 | 30 | 22 | B | 68,000 | 148 | 147,000 (1.51) | 0 | 2.4 | 3.0 | 85 |
| 0.56 | | | 5 | 60 | 60 | 157 | A | 28,000 | 136 | 115,000 (1.10) | 0 | 1.1 | 1.1 | 8.9 |
| 6.0 | 4-CH$_3$ | Zr | 5 | 30 | 60 | 12 | B | 20,000 | 128 | 60,000 (0.586) | 0 | 2.9 | 7.3 | 67 |
| 2.1 | | | 5 | 60 | 60 | 62 | A | 30,000 | 112 | 42,009 (0.850) | 0 | 2.7 | 3.0 | 76 |
| 5.0 | 1-OCH$_3$ | Zr | 5 | 30 | 60 | 40 | B | 8,000 | 142 | 76,000 (1.08) | 0 | 0.75 | 1.3 | 89 |
| 1.0 | | | 5 | 60 | 60 | 21 | A | 21,000 | 136 | 77,000 (0.957) | 0 | 1.8 | 4.1 | |
| 2.0 | 2-OCH$_3$ | Zr | 5 | 30 | 60 | 65 | B | 3,000 | 134 | 103,000 (1.37) | 0 | 1.1 | 3.5 | 82 |
| 1.0 | | | 5 | 60 | 60 | 3 | A | 3,000 | 129 | 50,000 (0.810) | | | | |
| 2.0 | | | 5 | 60 | 60 | 163 | A | 8,000 | 117 | 69,000 (1.02) | 0 | 1.7 | 7.7 | 75 |
| 1.0 | 3-OCH$_3$ | Zr | 5 | 30 | 60 | 30 | B | 3,000 | 141 | 114,000 (1.42) | 0 | 1.3 | 2.0 | 87 |

TABLE I-continued

| Catalyst (mg) | Substituent | Metal | MAO (ml) | Polymerization Temp (°C.) | Time (min) | Yield (g) | Method | Catalyst Efficiency (g/g · hr) | Melting Point (°C.)[a] | Molecular Weight* | NMR Data (%)[g] mmmm | rmmr | xmrx | rrrr |
|---|---|---|---|---|---|---|---|---|---|---|---|---|---|---|
| 2.0 | | | 5 | 60 | 60 | 72 | A | 4,000 | 131 | 72,000 (1.05) | 0 | 1.8 | 4.3 | 82 |
| 0.65 | 4-OCH₃ | Zr | 5 | 20 | 60 | 20 | B | 31,000 | 147 | 331,000 (2.41) | 0 | 0.76 | 1.5 | 88 |
| 0.35 | | | 5 | 30 | 45 | 30 | B | 38,000 | 146 | 295,000 (1.84) | 0 | 1.8 | 4.1 | 80 |
| 0.56 | | | 5 | 60 | 60 | 137 | A | 25,000 | 136 | 189,000 (1.67) | | | | |
| 0.51 | | | 0 | 60 | 86 | 86 | C[b] | 172,000 | 127 | 85,000 | | | | |
| 5.0 | 4-OCH₃ | Hf | 5 | 30 | 60 | 5 | B | 1,000 | n.d. | 676,000 (4.79) | | | | |
| 5.0 | | | 5 | 60 | 60 | 50 | A | 1,000 | n.d. | 447,000 (3.64) | 0 | 2.3 | 9.5 | 68 |
| 2.5 | | | 0 | 50 | 60 | 5 | C | 2,000 | n.d. | 1,021,000 | 0 | 9.8 | 3.3 | 52 |
| 0.75 | 2,7-(C≡CC(CH₃)₃)₂ | Zr | 5 | 50 | 60 | 10 | A | 13,000 | 129 | 84,000 (1.05) | 0 | 2.0 | 5.8 | 80 |
| 2.0 | 2,7-(C(CH₃)₃)₂* | Zr | 5 | 30 | 60 | 53 | A | 26,500 | 149 | 119,000 | 0 | 1.0 | 0.31 | 92 |
| 0.5 | | | 5 | 50 | 60 | 54 | A | 108,000 | 146 | 98,000 | | | | |
| 0.5 | | | 5 | 60 | 60 | 58 | A | 116,000 | 141 | 75,000 | 0 | 1.3 | 1.8 | 85 |
| 0.5 | | | 5 | 70 | 60 | 56 | A | 112,000 | 136 | 62,000 | | | | |
| 2.0 | H** | Zr | 5 | 30 | 60 | 23 | A | 11,500 | 140 | 963,000 | 0 | 1.2 | 0.61 | 90 |
| 2.0 | | | 5 | 50 | 60 | 60 | A | 60,000 | 137 | 696,000 | | | | |
| 2.0 | | | 5 | 60 | 60 | 54 | A | 108,000 | 131 | 507,000 | 0 | 1.8 | 1.8 | 87 |
| 2.0 | | | 5 | 70 | 60 | 44 | A | 44,000 | 128 | 309,000 | | | | |
| 0.65 | 2,7-[C(CH₃)₃]₂** | Zr | 5 | 30 | 60 | 47 | A | 37,000 | 144 | 671,000 | | | | |
| 0.75 | | | 5 | 60 | 60 | 112 | A | 63,000 | 137 | 370,000 (3.01) | | | | |
| 1.0 | | | 5 | 50 | 60 | 48 | A | 48,000 | 139 | 440,000 | | | | |
| 5.0[e] | 4-OCH,3 | | 5 | 30 | 60 | 30 | B | 12,000 (est) | 144 | 124,000 (1.44) | 0 | 0.81 | 2.5 | 90 |
| 10.0[e] | 2,7-C(CH₃)₃ | | 5 | 60 | 60 | 246 | A | 50,000 (est) | 128 | 107,000 (1.32) | 0 | 0.89 | 5.8 | 82 |
| 3.0[e] | 4-CH₂OCH₃ | Zr | 5 | 60 | 30 | 19 | A | 12,000 (est) | 94 | 92,000 | 0 | 2.9 | 4.9 | 74 |
| 3.0[e] | | | 5 | 30 | 60 | 27 | B | 9,000 (est) (120)[d] | 127 | 79,000 (1.16) | 1.6 | 3.9 | 9.7 | 56 |
| 1.0 | 2,7-(CH₃)₂ | Zr | 5 | 30 | 60 | 21 | B | 21,000 | 142 | 141,00 (1.52) | 0 | 0.88 | 1.5 | 86 |
| 0.55 | | | 5 | 60 | 60 | 62 | A | 109,000 | 135[d] | 126,000[d] | 0 | 1.8 | 4.1 | 84 |
| 6.5[e] | 2,7-Cl₂ | Zr | 10 | 60 | 60 | 55 | A | 8,500 (est) | 136 (132)[e] | 68,000 (0.943) | 0 | 2.2 | 4.1 | 80 |
| 2.0 | 2,7-F₂ | | 5 | 30 | 60 | 11 | A | 5,500 | 141 | 146,000 (1.43) | | | | |
| 1.0 | | | 5 | 60 | 60 | 98 | A | 98,000 | 132 | 83,000 (1.01) | | | | |
| 0.5 | | | 5 | 70 | 60 | 54 | A | 108,000 | 125 | 69,000 (0.943) | | | | |
| 8.0 | 2,7-[N(CH₃)₂]₂ | Zr | 5 | 60 | 60 | 0 | A | — | — | — | | | | |
| 5.0 | | | 0 | 60 | 30 | 0 | D | — | — | — | | | | |
| 5.0 | | | 0 | 60 | 30 | 0 | C | — | — | — | | | | |
| 5.1 | 2-N(CH₃)₂ | Zr | 5 | 30 | 30 | 4 | B | 800 | n.d. | — | | | | |
| 5.1 | | | 5 | 60 | 60 | 13 | A | 2,500 | n.d. | — | 2.3 | 6.2 | 22 | 18 |
| 5.0 | 4-N(CH₃)₂ | Zr | 5 | 30 | 60 | 106 | B | 21,000 | n.d. | 157,000 (1.58) | 3.0 | 7.2 | 23 | 14 |
| 5.0 | | | 5 | 60 | 60 | 46 | A | 9,200 | n.d. | 169,000 (1.46) | 3.0 | 5.5 | 23 | 14 |

*Gel Permeation Chromatographyl intrinsic viscosity valve is given in parenthesis in dL/g for a Decalin (decahydronaphthalene) solution at 135° C.
**bridge = diphenylmethyl [C(C₆H₅)₂]
[a]by DSC, higher of two melting points observed for the polymer is reported.
[b]6.00 mg [Trityl][B(C₆F₅)₄] and 2.0 mmol TEAL was used.
[c]Contains LiCl and possibly coordinated oxygen containing solvents.
[d]Polymer recrystallized three times from xylenes.
[e]Catalyst prepared according to the procedure of Mitsui Toatsu Corporation, Japan revealed via an internal communication.
[f]Catalyst prepared according to the procedure described in a Hoechst AG patent application. (Japan Kokai JP90-274,703; DE 907,965.1)
[g]¹³CNMR spectra of the polymers were run at 120° C. on Varian VXR3005 spectrometer using 20% (W/W) solutions of the polymers in 1,2,4-trichlorobenzene/d₆-benzene. The peak analysis and curve fitting was done with NMRI software package.

H-iPr(Flu)(Cp)ZrCl$_2$-isopropyl (fluorenyl) (cyclopentadienyl) zirconium dichloride 4-CH$_3$-iPr(4-CH$_3$Flu) (Cp) ZrCl$_2$-isopropyl (4-methylfluorenyl) (cyclopentadienyl)zirconium dichloride 1-OCH$_3$-iPr(1-OCH$_3$Flu) (Cp) ZrCl$_2$-isopropyl (1-methoxyfluorenyl) (cyclopentadienyl ) zirconium dichloride 2-OCH$_3$-iPr(2-OCH$_3$Flu) (Cp) ZrCl$_2$-isopropyl (2-methoxyfluorenyl) (cyclopentadienyl)zirconium dichloride 3-OCH$_3$-iPr(3-OCH$_3$Flu) (Cp) ZrCl$_2$-isopropyl (3-methoxyfluorenyl) (cyclopentadienyl)zirconium dichloride 4-OCH$_3$(Zr) -iPr(4-OCH$_3$Flu) (Cp) ZrCl$_2$-isopropyl (4-methoxyfluorenyl) (cyclopentadienyl)zirconium dichloride 4-OCH$_3$(Hf) -iPr(4-OCH$_3$Flu) (Cp) H$_f$Cl$_2$-isopropyl (4-methoxyfluorenyl) (cyclopentadienyl) Hafnium dichloride 2,7-(C≡CC(CH$_3$)$_3$)$_2$-iPr[2,7-(C≡CC(CH$_3$)$_3$)$_2$Flu][Cp]ZrCl$_2$-isopropyl (2,7-di(t-butylethynylfluorenyl (cyclopentadienyl) zirconium dichloride 2,7-(C(CH$_3$)$_3$)$_2$-iPr(2,7-di(C(CH$_3$)$_3$)$_2$Flu) (Cp) ZrCl$_2$-isopropyl (2,7-di-t-hutylfluorenyl) (cyclopentadienyl) zirconium dichloride H, bridge=C(C$_6$H$_5$)$_2$-C(C$_6$H$_5$)$_2$(Flu) (Cp) ZrCl$_2$-diphenylmethyl (fluorenyl) (cyclopentadienyl)zirconium dichloride 2,7-(C(CH$_3$)$_3$)$_2$, bridge=[C(CH$_3$)$_3$]$_2$-C(C$_6$H$_5$)$_2$(2,7-di(C(CH$_3$)$_3$)$_2$(Flu) (Cp) ZrCl$_2$-diphenylmethyl (2,7-di-t-butylfluorenyl) (cyclopentadienyl) zirconium dichloride 4-OCH$_3$, 2,7-C(CH$_3$)$_3$-iPr(4-OCH$_3$, 2,7-[(CH$_3$)$_3$]$_2$Flu) (Cp) ZrCl$_2$-isopropyl (4-methoxy-2,7-di-t-butylfluorenyl) (cyclopentadienyl) zirconium dichloride 4-CH$_2$OCH$_3$-iPr(4-CH$_2$OCH$_3$Flu)(Cp)ZrCl$_2$ -isopropyl(4-methoxymethylfluorenyl) (cyclopentadienyl)zirconium dichloride 2,7-(CH$_3$)$_2$-iPr(2,7-(CH$_3$)$_2$(Flu)(Cp)ZrCl$_2$ -isopropyl(2,7-dimethylfluorenyl) (cyclopentadienyl)zirconium dichloride 2,7-Cl$_2$-iPr(2,7-Cl$_2$Flu)(Cp)ZrCl$_2$-isopropyl(2,7-dichlorofluorenyl) (cyclopentadienyl)zirconium dichloride 2,7-F$_2$-iPr(2,7-(F$_2$)Flu)(Cp)ZrCl$_2$-isopropyl(2,7-difluorofluorenyl) (cyclopentadienyl)zirconium dichloride 2,7-[(N(CH$_3$)$_2$]$_2$-iPr(2,7-[N(CH$_3$)$_2$]$_2$(Flu) (Cp) ZrCl$_2$-isopropyl (2,7-bis-dimethylaminofluorenyl) (cyclopentadienyl)zirconium dichloride 2,7-[(N(CH$_3$)$_2$]$_2$-iPr(2,7-[N(CH$_3$)$_2$]$_2$(Flu)(Cp)Zr(CH$_3$)$_2$-isopropyl(2,7-bis-dimethylaminofluorenyl) (cyclopentadienyl)zirconium dimethyl 2-N(CH$_3$)$_2$-iPr(2-N(CH$_3$)$_2$Flu)(Cp)ZrCl$_2$-isopropyl(2-dimethylaminofluorenyl) (cyclopentadienyl)zirconium dichloride 4-N(CH$_3$)$_2$-iPr(4-N(CH$_3$)$_2$(Flu)(Cp)ZrCl$_2$-isopropyl(4-dimethylaminofluorenyl) (cyclopentadienyl)zirconium dichloride The results shown in Table I illustrate some of the advantages of the present invention. The compositions and locations of the substituents on the aryl rings of fluorene do have a significant influence on the stereoregularities, melting points and the molecular weights of the polymers. These effects are a result of the steric and electronic properties of the substituents.

Substituents which are electron donating, either inductively or via resonance, increase the basicity of fluorene in the catalyst. This has been documented in the "J. Org. Chem.", 41, 2391 (1976). It is believed that increasing the basicity of the fluorene ring by substitution increases the catalyst activity. Substituents which increase the basicity of the fluorene ring include alkyl, alkylamino and alkoxy groups.

The present invention clearly shows that electron donating substituents, for example, dialkylamino, halogen, and alkoxy groups, when present on fluorene at C1, C2, C3 or C2 and C7 render the catalyst less active than the unsubstituted complex. The polymers obtained with the catalysts containing these groups also, generally, have lower molecular weights. This behavior of the catalyst is contrary to expectations.

The Applicants theorize, without limiting the scope of the claims, that the mechanism is due to the Lewis acid-base complexation with the cocatalysts such as either MAO or trimethyl aluminum, which is often present as an impurity in MAO, or [Ph$_3$C][B(C$_6$F$_5$)$_4$] or Bronsted acid-base interactions with cocatalysts such as [(C$_6$H$_5$)N(CH$_3$)$_2$H] [B(C$_6$F$_5$)$_4$]. When the lone pair of electrons on the nitrogen or oxygen atom, directly attached to the fluorene ring are used in complexation to an acidic center, a positive charge is created on the heteroatom. As a consequence, the positive center withdraws electrons away from fluorene thus drastically decreasing its basicity. This results in low polymerization efficiencies and low polymer molecular weights.

This effect is even more dramatic in the case of iPr[2,7-[N(CH$_3$)$_2$]$_2$Flu)(Cp)ZrCl$_2$ wherein the lone pairs of electrons on both the nitrogens are tied up in complexation to the cocatalysts, thus suppressing the electron donating (through resonance) ability and increasing the electron withdrawing (through induction) of nitrogen. Similar reasoning can explain decrease in catalyst activities and polymer molecular weights with catalysts containing basic oxygen atoms on C1, C2 or C3 of fluorene.

Non-coordinating, but weak electron donating substituents, such as alkyl groups, on fluorene are capable of decreasing the basicity of fluorene only slightly. The dimethyl group at C2 and C7 did not affect the catalyst efficiency and molecular weight significantly but the t-butyl group decreased the molecular weight while not decreasing the catalyst activity. The ability of the electron donating substituent to donate electrons must be equal to or greater than that for t-butyl, dimethylamino, chlorine, fluorine or methoxy to decrease the molecular weight.

The invention also discloses some unique features of the effects on polymer molecular weight of C4 substitution of fluorene. While an electron donating substituent, such as alkyl, dialkylamino, halogen or alkoxy, at C1, C2 or C3 of fluorene decreases the catalyst efficiency, the same substituent at C4 not only increased the catalyst efficiency but also dramatically increased the polymer molecular weight. Weak electron donating substituents, such as alkyl or alkoxyalkyl, do not have the same effect. It is theorized, without limiting the scope of the claims, that the heteroatoms when present at C4/C5 on fluorene are in a sterically inaccessible region, thus preventing or minimizing coordination with the cocatalyst. The heteroatoms appear to be able to donate electrons through resonance to fluorene thus increasing its basicity and resulting in an increase in molecular weight.

In summary, to increase the catalyst activity and polymer molecular weight, substituents which are either electron donating, non-coordinating groups or heteroatoms bonded to sterically encumbered carbons capable of preventing complexation of the acidic cocatalyst needed to be present on the fluorene ring. Specifically, increased catalyst activity and polymer molecular weights can be realized by substituting fluorene at C4/C5 with heteroatoms capable of electron donation through resonance and decreased catalyst activity and polymer molecular weights can be obtained by substituting fluorene with electron withdrawing groups. The ability of the electron donating substituent to donate electrons must be equal to or greater than that for methoxy or dimethylamino.

The present invention also addresses the effect of fluorene substituents on the melting point of the polymer. Generally, the melting point of the polymer is a reflection of the tacticity of the polymer. The higher the syndiotacticity of the polymer, the higher is the melting point. Some of the factors which affect the polymer melting point include catalyst and cocatalyst structure and polymerization conditions. Present invention clearly reveals that the stereoregulation during polymerization is strongly influenced by the nature of the substituent, and its location on fluorene. Bulky hydrocarbyl substituents, such as alkyl, cycloalkyl and aryl groups, at C2 and C7 increase the polymer tacticity and as a consequence its melting point. Smaller groups at C2 and C7 such as an oxygen, chlorine or fluorine do not affect the tacticity or the melting point of the polymer. Methyl groups at C2 and C7 did not increase the tacticity of the polymer significantly. The substituent effects at C2 and C7 on polymer melting point appears to be due to the bulky substituents at C2 and C7 assisting in the termination of polymer chain growth when the catalyst makes specific mistakes resulting in shorter chain length for the polymer and higher tacticity and melting point. T-butyl groups at C2 and C7 yielded polymer with increased melting points compared to polymer produced with an unsubstituted catalyst. Substituting groups at C2 and C7 which are as least as bulky as t-butyl increases the tacticity and melting point above that for polymer produced with an unsubstituted catalyst. Other hydrocarbyl groups or non-coordinating substituents larger than a t-butyl group are expected to increase polymer tacticity in direct proportion to their size.

Bulky substituents such as hydrocarbyl groups like alkyl, cycloalkyl, aryl, alkoxy and dialkylamino groups etc., at C4/C5 decrease the polymer tacticity and as a consequence its melting point. Smaller groups at C4/C5 such as an oxygen atom or fluorine do not affect the tacticity or the melting point of the polymer. The substituent effects at C4/C5 on polymer melting point appears to be due to the negative interference of the bulky groups at C4/C5 with monomer coordination. Theoretical calculations published in the literature suggest that propylene coordinates to zirconium in such a way that the methyl group protrudes into the C4/C5 region. The effect on polymer melting point of substituents elsewhere on fluorene depended primarily on their size, provided that such substituents do not interact with the cocatalyst independently. Hydrocarbyl groups such as alkyl, cycloalkyl and aryl groups are particularly suitable because they are non-coordinating and their size can be varied easily. Substituting groups at C4/C5 which are as least as bulky as methoxy or dimethylamino decreases the tacticity and melting point below that for polymer produced with an unsubstituted catalyst.

The present invention also shows that when multiple substituents are present on fluorene, their effects are additive. Thus, for example, if a small electron donating group is present at C4/C5 and bulky non-coordinating groups such as alkyl, cycloalkyl, arylalkyl groups or such derivative of group IV elements such as Si, Ge and Sn are present on C2, C3, C2 and C7 or C3 and C6, their overall effects on the polymer would be to increase the polymer molecular weight as well as its tacticity and hence its melting point.

It is noted that the polymerization temperature is a factor in the formulation of the polymer product. At the lower reaction temperatures, the melting points and molecular weights for the same catalyst were higher. As the reaction temperatures increased, the melting points and the molecular weights decreased. Also, as the reaction temperature increased, the yields and catalyst efficiencies also increased, usually dramatically. However, it is noted that the effect of type and location of substituent is independent of the polymerization temperature.

Some of the advantages of the present invention are realized by comparing the polymer properties of Examples using different catalysts but run at the same polymerization temperature. In making these comparisons, it can be seen that the melting points and molecular weights increased when appropriate substituents were in position 4. Also, the molecular weight increased when a Lewis base, such as oxygen, is directly connected to the 4-carbon on the aryl ring. The results show that polymers with lower molecular weights are produced by catalysts with substituents in position other than position 4. Substituents in positions 2 and 7 increased the melting point but decreased the molecular weight. The results clearly show that the melting points and molecular weights can be varied and controlled by changing the substituent groups on the aryl rings of the fluorene ligand.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States is:

1. A catalyst system for polymerizing propylene to produce a syndiotactic polypropylene comprising:

a) a metallocene of the general formula:

wherein $(C_5H_4)$ is a cyclopentadienyl ring and $(C_4H_{4-m}R'_mC_5C_4H_{4-n}R'_n)$ is a fluorenyl radical; R' is a hydrocarbyl radical, halogen, an alkoxy, an alkoxy alkyl or an alkylamino radical having from 1-20 carbon atoms, each R' may be the same or different; R" is a structural bridge between the $(C_5H_4)$ and $(C_4H_{4-m}R'_mC_5C_4H_{4-n}R'_n)$ rings to impart stereorigidity; Q is a hydrocarbon radical or a halogen; Me is a Group IVB metal; $1 \leq m \leq 4$; $0 \leq n \leq 4$; and p is the valence of Me minus 2;

wherein R' is an electron donating substituent on the fluorene ligand at C1, C2, or C3 and has the ability to donate electrons equal to or greater than that for methoxy;

b) a co-catalyst selected from the group consisting of an organoaluminum compound of the general formula (R-Al-O) in the cyclic form or $R(R-Al-O)_nAlR_2$ in the linear form wherein R is an alkyl group with 1-5 carbons and n is an integer from about 1 to about 20, a neutral Lewis acid and an ionic ionizing agent.

2. A catalyst system as recited in claim 1 wherein the organoaluminum compound is methylalumoxane.

3. A catalyst system as recited in claim 1 wherein the ionic ionizing agent is selected from the group consisting of triphenylcarbenium tetrakis(pentafluorophenyl) boronate and N,N-dimethylanilinium tetrakis(pentafluorophenyl) boronate.

4. A catalyst system as recited in claim 1 wherein the co-catalyst is a Lewis acid or an ionic ionizing agent and additionally comprises an aluminum alkyl.

5. A catalyst system as recited in claim 1 wherein R' is selected from the group consisting of alkoxy groups.

6. A catalyst system as recited in claim 1 wherein the metallocene compound is selected from the group consisting of isopropylidene(1-methoxyfluorenyl)(cyclopentadienyl) zirconium dichloride, isopropylidene(2-methoxyfluorenyl) (cyclopentadienyl) zirconium dichloride and isopropylidene (3-methoxyfluorenyl) (cyclopentadienyl)zirconium dichloride.

7. A catalyst system as recited in claim 1 wherein R" is an alkylidene radical having 1–4 carbon atoms, or arylalkylidene or aryl alkylidene radical containing 7–20 atoms, a silicon hydrocarbyl radical, a germanium radical, an alkyl phosphine, or an alkyl amine.

8. A catalyst system as recited in claim 7 wherein R" is methylidene, ethylidene, isopropylidene, diarylmethylidene, an alkyl silylidene or a cycloalkyl silylidene.

9. A catalyst system as recited in claim 8 wherein R" is isopropylidene or diphenylmethylidene.

10. A catalyst system as recited in claim 1 wherein Me is selected from the group consisting of zirconium and hafnium.

11. A catalyst system as recited in claim 1 wherein Q is methyl, ethyl, propyl, butyl, amyl, isoamyl, hexyl, isobutyl, heptyl, octyl, nonyl, decyl, cetyl, phenyl, fluorine, chlorine, bromine or iodine.

12. A catalyst system as recited in claim 11 wherein Q is chlorine or methyl.

13. A catalyst system for polymerizing propylene to produce a syndiotactic polypropylene comprising:

a) a metallocene of the general formula:

wherein $(C_5H_4)$ is a cyclopentadienyl ring and $(C_4H_{4-m}R'_mC_5C_4H_{4-n}R'_n)$ is a substituted cyclopentadienyl ring; R' is a hydrocarbyl radical, halogen, an alkoxy, an alkoxy alkyl or an alkylamino radical having from 1–20 carbon atoms, each R' may be the same or different; R" is a structural bridge between the $(C_5H_4)$ and $(C_4H_{4-m}R'_mC_5C_4H_{4-n}R'_n)$ rings to impart stereorigidity; Q is a hydrocarbon radical; Me is a Group IVB metal as positioned in the Periodic Table of Elements; $1 \leq m \leq 4$; $0 \leq n \leq 4$; and p is the valence of Me minus 2; wherein R' is an electron donating substituent on the fluorene ligand at C4 or C5 and has the ability to donate electrons equal to or greater than that for a dimethylamino or methoxy;

b) a co-catalyst selected from the group consisting of an organoaluminum compound of the general formula (R-Al-O) in the cyclic form and R(R-Al-O)$_n$AlR$_2$ in the linear form wherein R is an alkyl group with 1–5 carbons and n is an integer from 1 to about 20, a neutral Lewis acid and an ionic ionizing agent.

14. A catalyst system as recited in claim 13 wherein the organoaluminum compound is methylalumoxane.

15. A catalyst system as recited in claim 13 wherein the ionic ionizing agent is selected from the group consisting of triphenylcarbenium tetrakis(pentafluorophenyl) boronate and N,N-dimethylanilinium tetrakis(pentafluorophenyl) boronate.

16. A catalyst system as recited in claim 13 wherein the co-catalyst is a Lewis acid or an ionic ionizing agent and additionally comprises an aluminum alkyl.

17. A catalyst system as recited in claim 13 wherein the metallocene compound is selected from the group consisting of isopropylidene(4-methoxyfluorenyl)(cyclopentadienyl) zirconium dichloride, isopropylidene(4-methoxyfluorenyl) (cyclopentadienyl)hafnium dichloride and isopropylidene (4-dimethylaminofluorenyl) (cyclopentadienyl)zirconium dichloride.

18. A catalyst system as recited in claim 13 wherein R" is an alkylidene radical having 1–4 carbon atoms, or arylalkylidene or diaryl alkylidene radical containing 7–20 atoms, a silicon hydrocarbyl radical, a germanium hydrocarbyl radical, an alkyl phosphine, or an alkyl amine.

19. A catalyst system as recited in claim 18 wherein R" is methylidene, isopropylidene, diarylmethylidene, an alkyl silylidene or a cycloalkyl silylidene.

20. A catalyst system as recited in claim 19 wherein R" is isopropylidene.

21. A catalyst system as recited in claim 13 wherein Me is selected from the group consisting of zirconium and hafnium.

22. A catalyst system as recited in claim 13 wherein Q is methyl, ethyl, propyl, butyl, amyl, isoamyl, hexyl, isobutyl, heptyl, octyl, nonyl, decyl, cetyl, phenyl, fluorine, chlorine, bromine or iodine.

23. A catalyst system as recited in claim 22 wherein Q is chlorine or methyl.

24. A catalyst system as recited in claim 13 wherein R' is selected from the group consisting of dialkylamino, and alkoxy groups.

25. A catalyst system for polymerizing propylene to produce a syndiotactic polypropylene comprising:

a) a metallocene of the general formula:

wherein $(C_5H_4)$ is a cyclopentadienyl ring and $(C_4H_{4-m}R'_mC_5C_4H_{4-n}R'_n)$ is a substituted cyclopentadienyl ring; R' is a hydrocarbyl radical, halogen, an alkoxy, an alkoxy alkyl or an alkylamino radical having from 1–20 carbon atoms, each R' may be the same or different; R" is a structural bridge between the $(C_5H_4)$ and $(C_4H_{4-m}R'_mC_5C_4H_{4-n}R'_n)$ rings to impart stereorigidity; Q is a hydrocarbon radical; Me is a Group IVB metal as positioned in the Periodic Table of Elements; $1 \leq m \leq 4$; $0 \leq n \leq 4$; and p is the valence of Me minus 2; wherein R' is a bulky substituent present on the fluorene ligand at C4 or C5 and is as least as bulky as methoxy or dimethylamino;

b) a co-catalyst selected from the group consisting of an organoaluminum compound of the general formula (R-Al-O) in the cyclic form and R(R-Al-O)$_n$AlR$_2$ in the linear form wherein R is an alkyl group with 1–5 carbons and n is an integer from 1 to about 20, a Lewis acid and an ionic ionizing agent.

26. A catalyst system as recited in claim 25 wherein the organoaluminum compound is methylalumoxane.

27. A catalyst system as recited in claim 25 wherein R' is selected from the group consisting of alkyl, cycloalkyl, aryl, alkoxy and dialkylamino groups.

28. A catalyst system as recited in claim 25 wherein the metallocene compound is isopropylidene(4-methoxyfluorenyl) (cyclopentadienyl) zirconium dichloride, isopropylidene(4-methoxymethylfluorenyl) (cyclopentadienyl)zirconium dichloride or isopropylidene (4-dimethylaminofluorenyl)(cyclopentadienyl)zirconium dichloride.

29. A catalyst system as recited in claim 25 wherein R" is an alkylidene radical having 1–4 carbon atoms, or arylalkylidene or diaryl alkylidene radical contains 7–20 atoms, a silicon hydrocarbyl radical, a germaniumhydrocarbyl radical, an alkyl phosphine, or an alkyl amine.

30. A catalyst system as recited in claim 29 wherein R" is methylidene, isopropylidene, diarylmethylidene, an alkyl silylidene or a cycloalkyl silylidene.

31. A catalyst system as recited in claim 30 wherein R" is isopropylidene.

32. A catalyst system as recited in claim 25 wherein Me is selected from the group consisting of zirconium and hafnium.

33. A catalyst system as recited in claim 25 wherein Q is methyl, ethyl, propyl, butyl, amyl, isoamyl, hexyl, isobutyl, heptyl, octyl, nonyl, decyl, cetyl, phenyl, fluorine, chlorine, bromine or iodine.

34. A catalyst system as recited in claim 33 wherein Q is chlorine or methyl.

35. A catalyst system for polymerizing propylene to produce a syndiotactic polypropylene comprising:
   a) a metallocene of the general formula:

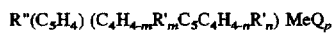

wherein (C$_5$H$_4$) is a cyclopentadienyl ring and (C$_4$H$_{4-m}$R'$_m$C$_5$C$_4$H$_{4-n}$R'$_n$) is a fluorenyl radical; R' is a hydrocarbyl radical, halogen, an alkoxy, an alkoxy alkyl or an alkylamino radical having from 1–20 carbon atoms, each R' may be the same or different; R" is a structural bridge between the (C$_5$H$_4$) and (C$_4$H$_{4-m}$R'$_m$C$_5$C$_4$H$_{4-n}$R'$_n$) rings to impart stereorigidity; Q is a hydrocarbon radical or a halogen; Me is a Group IVB metal; $1 \leq m \leq 4$; $0 \leq n \leq 4$; and p is the valence of Me minus 2;
   wherein R' is an electron donating substituent on the fluorene ligand at both C2 and C7 and has the ability to donate electrons equal to or greater than that for a dialkylamino or halogen;
   b) a co-catalyst selected from the group consisting of an organoaluminum compound of the general formula (R-Al-O) in the cyclic form and R(R-Al-O)$_n$AlR$_2$ in the linear form wherein R is an alkyl group with 1–5 carbons and n is an integer from about 1 to about 20, a Lewis acid and an ionic ionizing agent.

36. A catalyst system as recited in claim 35 wherein the metallocene is selected from the group consisting of isopropylidene (2,7-dichlorofluorenyl) (cyclopentadienyl) zirconium dichloride, isopropylidene (2,7-difluorofluorenyl) (cyclopentadienyl)zirconium dichloride, isopropylidene (2,7-di-methylamino-fluorenyl) (cyclopentadienyl) zirconium dichloride and isopropylidene (2,7-dimethylaminofluorenyl) (cyclopentadienyl) zirconium dimethyl.

37. A catalyst system as recited in claim 35 wherein the ionic ionizing agent is selected from the group consisting of triphenylcarbenium tetrakis (pentafluorophenyl) boronate and N,N-dimethylanilinium tetrakis (pentafluorophenyl) boronate.

38. A catalyst system as recited in claim 35 wherein the co-catalyst is a Lewis acid or an ionic ionizing agent and additionally comprises an aluminum alkyl.

39. A catalyst system as recited in claim 35 wherein R' is selected from the group consisting of dimethylamino, chlorine and fluorine.

40. A catalyst system as recited in claim 35 wherein R" is an alkylidene radical having 1–4 carbon atoms, or arylalkylidene or diarylalkylidene radical containing 7–20 atoms, a silicon hydrocarbyl radical, a germanium hydrocarbyl radical, an alkyl phosphine, or an alkyl amine.

41. A catalyst system as recited in claim 40 wherein R" is methylidene, ethylidene, isopropylidene, diarylmethylidene, an alkyl silylidene or a cycloalkyl silylidene.

42. A catalyst system as recited in claim 41 wherein R" is isopropylidene or diphenylmethylidene.

43. A catalyst system as recited in claim 35 wherein Me is selected from the group consisting of zirconium and hafnium.

44. A catalyst system as recited in claim 35 wherein Q is methyl, ethyl, propyl, butyl, amyl, isoamyl, hexyl, isobutyl, heptyl, octyl, nonyl, decyl, cetyl, phenyl, fluorine, chlorine, bromine or iodine.

45. A catalyst system as recited in claim 44 wherein Q is chlorine or methyl.

* * * * *